(12) United States Patent
Hanko et al.

(10) Patent No.: US 10,078,077 B2
(45) Date of Patent: Sep. 18, 2018

(54) APPARATUS FOR AUTOMATED DETERMINING OF AT LEAST TWO DIFFERENT PROCESS PARAMETERS

(71) Applicant: Endress + Hauser Conducta Gesellschaft für Mess- und Regeltechnik mbH + Co. KG, Gerlingen (DE)

(72) Inventors: Michael Hanko, Dresden (DE); Angela Eubisch, Chemnitz (DE)

(73) Assignee: Endress+Hauser Conducta Gmbh+Co. KG, Gerlingen (DE)

( * ) Notice: Subject to any disclaimer, the term of this patent is extended or adjusted under 35 U.S.C. 154(b) by 738 days.

(21) Appl. No.: 14/283,425

(22) Filed: May 21, 2014

(65) Prior Publication Data
US 2014/0356880 A1    Dec. 4, 2014

(30) Foreign Application Priority Data
May 28, 2013 (DE) .................... 10 2013 105 492

(51) Int. Cl.
*C12Q 3/00* (2006.01)
*G01N 33/53* (2006.01)
*C12Q 1/00* (2006.01)

(52) U.S. Cl.
CPC ........... *G01N 33/5308* (2013.01); *C12Q 1/00* (2013.01); *C12Q 3/00* (2013.01)

(58) Field of Classification Search
None
See application file for complete search history.

(56) References Cited

U.S. PATENT DOCUMENTS

| 3,846,243 A | 11/1974 | Furner |
| 5,262,961 A | 11/1993 | Farone |

(Continued)

FOREIGN PATENT DOCUMENTS

| CN | 102391995 A | 3/2012 |
| CN | 102732423 A | 10/2012 |

(Continued)

OTHER PUBLICATIONS

German Search Report, DPMA, Munich, dated Feb. 27, 2014.

*Primary Examiner* — Rebecca L Martinez
(74) *Attorney, Agent, or Firm* — Mark A. Logan; PatServe

(57) ABSTRACT

An apparatus for automated determining of at least two different process parameters of a process liquid of a process, especially a bioprocess, comprising: a first measuring cell, which is embodied to provide a first measurement signal dependent on a first process parameter of a first sample of the process liquid; a second measuring cell, which is embodied to provide a second measurement signal dependent on a second process parameter of a second sample of the process liquid; and a control and evaluation system, which serves for monitoring and/or controlling the process, and which is embodied to receive and to process the first and second measurement signals, especially based on the first measurement signal to determine a measured value of the first process parameter and based on the second measurement signal to determine a measured value of the second process parameter; wherein the first measurement signal and the second measurement signal serve different functions in the context of the monitoring and/or controlling of the process. The first process parameter can be a control parameter (critical process parameter, CPP), and the second process (Continued)

parameter can be a product quality parameter (critical quality attribute, CQA) of the process.

16 Claims, 2 Drawing Sheets

(56) References Cited

U.S. PATENT DOCUMENTS

| | | | |
|---|---|---|---|
| 8,900,855 | B2 | 12/2014 | Feng |
| 2005/0208473 | A1 | 9/2005 | Krichevsky |
| 2007/0224702 | A1 | 9/2007 | Inganas |
| 2007/0292958 | A1 | 12/2007 | Lacourse |
| 2008/0241966 | A1 | 10/2008 | Kunnecke |
| 2011/0159475 | A1* | 6/2011 | West ................ C12M 41/48 435/3 |
| 2013/0217003 | A1 | 8/2013 | Hanko |

FOREIGN PATENT DOCUMENTS

| | | |
|---|---|---|
| CN | 102231057 A | 9/2013 |
| CN | 103320484 A | 9/2013 |
| CN | 103339248 A | 10/2013 |
| DE | 3406223 A1 | 8/1984 |
| DE | 19612766 A1 | 10/1997 |
| DE | 102010064391 A1 | 5/2012 |
| KR | 100353893 B1 | 10/2002 |
| SU | 614029 | 7/1978 |

\* cited by examiner

APPARATUS FOR AUTOMATED DETERMINING OF AT LEAST TWO DIFFERENT PROCESS PARAMETERS

TECHNICAL FIELD

The invention relates to an apparatus and to a method for automated determining of at least two different process parameters in a sample of a process liquid of a process. The process can be a bioprocess. Especially, the invention relates to an apparatus and to a method for automated determining of a control parameter, e.g. a metabolite content, and a product quality parameter, e.g. a target protein content, of samples of the process liquid.

BACKGROUND DISCUSSION

A goal of (bio-)process analytics, above all, in the context of the PAT guideline of the FDA (US Food and Drug Administration), is lastly improving productivity while obtaining constant quality in the face of trying to shorten product introduction time. The acronym PAT stands for "Process Analytical Technology". The PAT guideline was created by the FDA as a stimulus and aid for optimizing, analysis and control of pharmaceutical manufacturing processes. The critical process parameters of a biopharmaceutical manufacturing process influencing the critical quality properties are to be analyzed and controlled corresponding to this guideline. The critical process parameters (per the PAT guideline, CPP for short) are control variables of the process, which enter into the corresponding control algorithms for process control. In the following, these parameters are also referred to as control parameters. To be distinguished therefrom are the parameters relevant to product quality (referred to in the PAT guideline as critical quality attributes, or CQA for short). These parameters serve as measures for product quality, but are not currently used as control parameters for the production process. The control parameters influence parameters relevant to product quality.

An example of the importance of bioprocess control is provided by the production of recombinant proteins. The heterologous gene expression is induced only after reaching a certain cell density. Within the two-phase cultivation process, consequently, both the cell growth as well as also the change to the metabolic phase, in which the product formation takes place, must be exactly monitored and controlled. Between cell growth and product production, which cannot be process dependently directly correlated with one another, a robust, reproducible process method/-regime must be determined by optimizing the cultivation conditions.

As explained, for example, in Rodrigues, M. E., Costa, A. R., Henriques, M. Azeredo, J., Oliveira, R. (2010). Technological progresses in monoclonal antibody production systems. *Biotechnol Prog*, 26 (2), Pgs. 332-351, an approach is the optimizing of the nutrient supply. In this regard, nutrients, especially metabolism educts, above all glucose, glutamine, and metabolism products, such as e.g. lactate, ammonium, glutamate, thus generally the metabolites, are to be reliably determined (Rodrigues et al., Pg. 343, left, 4th paragraph). The term, metabolite, means here and in the following not only a product or intermediate product of metabolism, but, instead, generally, a material participating in the metabolism, especially metabolism educts, intermediate products of metabolism and products of metabolism. Too low, however, also too high, metabolite concentrations (increased formation of toxic products) can lead to reduction of cell growth and/or productivity. Direct monitoring of the formed product would be extremely valuable and important for cell line selection and optimizing the cultivation parameters (Rodrigues et al. Pg. 343, right, 4th paragraph). A system, which within one and the same process-connected automation platform can exactly determine a number of critical process parameters, on the one hand, from the group of the metabolites and, on the other hand, from the group of the specific products, would be even more helpful.

The concept underpinning the PAT guideline aims to control the process by defining suitable control parameters, which are registered online, and thereby to achieve a desired product quality in a more efficient manner. Essential for the control of bioprocesses in the sense of the PAT-guideline is, consequently, the presence, respectively the development, of suitable online-enabled, sensor technology; i.e. sensors and process connected, analytical measurements technology.

Classic control parameters, especially also for the control of bioprocesses, include most often chemical/physical state variables, such as e.g. temperature, pH-value, $CO_2$, $O_2$ content, whose determination is established or at least possible by means of inline sensor technology. With biosensor-based measuring systems, other control parameters can be determined, which would not be accessible with classic, established measurements technology. Due to the instability of biological components, such systems have not proved themselves sufficient for routine inline use, so that for biosensor-based measuring systems the taking of a sample and delivery of such to a measuring cell is necessary. Biosensor determined control parameters include, for example, metabolites, thus nutrients or products of metabolism, whose content curve during a biological process has direct influence on the process control, in order to tune to optimal conditions for product manufacture—with the required quality.

The determining of product quality parameters, the CQAs, delivers direct information, whether the product has the required properties within an established tolerance range, especially a tolerance range defined by the relevant authorities for pharmaceutical production. Currently for determining the CQAs, samples taken daily manually from the process are examined in the laboratory following a lapse of time and, in such case, a multiplicity of product quality parameters are determined with corresponding laboratory analysis devices. Most often, only after process end are all samples examined together. The testing of the samples requires trained personnel for carrying out the involved tasks and for interpreting the results. A reaction to/handling of failure to achieve the desired product characteristics is not possible in the case of such a procedure.

Already known from the state of the art are some methods for determining individual CQAs and CPPs as well as commercially available analytical devices for performing these methods. These are set forth in the following Table I. In order that such devices can be applied in an automated manner in process measurements technology for monitoring, respectively for control of, production processes, a process connection is required, via which they can be connected with the process, in order to perform measurements, respectively remove samples from the process for the measurements. Table I indicates whether the respective analytical devices utilize a process connection.

TABLE I

| Method | Device | Prozess connection | CQA: product amount | CQA: product quality | CPP: metabolite |
|---|---|---|---|---|---|
| HPLC | e.g. UltiMate 3000 HPLC Systems (Thermo ScientificDionex, Thermo Fisher Scientific Inc., Waltham, MA, US) | no | yes | yes | no |
| ELISA | Most often, manual | no | yes | yes | no |
| Amperometric, enzyme sensors | YSI Flownamics SEG-FlOW (YSI Inc./Xylem Inc., Yellow Springs, Ohio, US) | yes (for laboratory-reactor) | no | no | yes |
| | Bioprofile-Analyzer (Nova Biomedical Corporation, Waltham, MA, US) | no | no | no | yes |
| | Biosensor-Arrays (Jobst Technologies GmbH, Freiburg, DE) | no | no | no | yes |
| | BioPAT Trace (Sartorius Stedim Biotech GmbH, Goettingen, DE) | yes (laboratory) | no | no | yes |
| Photometric | Konelab (Thermo Fisher Scientific, Inc., Waltham, MA, US), CuBiAn and Cedex Bio (F. Hoffmann-La Roche AG, Basel, CH) | no | yes (only Immunoglobuline) | no | yes |
| Separate lab devices united under a control unit | Baychromat Process/Lab (Bayer Technology Services GmbH, Leverkusen, DE) | yes (laboratory and process) | yes (only for Immunoglobuline as product) | no | yes |

Known from German Patent, EP 1698891 A1 is a method for reducing the measurement deviation of amperometric biosensors. This document concerns modifying the operation with potentials when an electrical mediator is applied as transmitting mediator of the actual redox reaction of the analyte. The systematic error of the so-called background current, above all, at the beginning of the reaction after storage and before application, is said to be reduced by the claimed procedure.

Described in German Patent, DE 3406223 A1 and U.S. Pat. No. 3,655,958 is an analytical device for automatically performing the standard addition method, wherein the US patent refers to spectral photometers.

Described in US Published Patent Application 2007/0224702 A1 is a method for determining a plurality of analytes in one or more samples, wherein each analyte is detected with its own affinity assay.

German Patent, DE 196 12 766 A1 describes a method for analysis of a complex biological system, in the case of which metabolism parameters are ascertained by means of ligand receptor interaction based on samples taken from a fermenter. Control of the process occurs via sensors arranged in the fermenter.

Known from German Patent, DE 10 2010 064 391 A1 is a method and an analytical device for automated determining of an analyte content of a liquid sample. This basically also permits detection of a number of different analytes in samples from a process liquid supplied one after the other to a measuring cell.

Described in Published Patent Application US 2005/0208473 A1 is a method for control of a bioprocess, in the case of which different control parameters are registered by sensors arranged in the bioreactor, among others, enzyme electrodes.

Known from Published Patent Application US 2007/0292958 A1 is an apparatus, in the case of which process liquid is removed from a fermentation process via a microdialysis probe and can be fed to an analytical apparatus for determining metabolite concentrations.

Described in Published Patent Application US 2008/0241966 A1 are a method and an apparatus, which are suitable for automated determining of various metabolites in a liquid sample.

SUMMARY OF THE INVENTION

An object of the invention is to provide an apparatus, respectively a method, of the field of the invention for avoiding disadvantages of the analytical devices and methods known from the state of the art. Especially, the apparatus and the method should enable monitoring and controlling processes, especially bioprocesses, according to the PAT guideline in an as energy and resource saving manner as possible.

This object is achieved by an apparatus for automated determining of at least two different process parameters of a process medium of a process, especially a bioprocess, including:
  a first measuring cell, which is embodied to provide a first measurement signal dependent on a first process parameter of a first sample of the process medium;
  a second measuring cell, which is embodied to provide a second measurement signal dependent on a second process parameter of a second sample of the process medium; and
  a control and evaluation system, which serves for monitoring and/or controlling the process, and which is embodied to receive and to process the first and second measurement signals, especially based on the first measurement signal to determine a measured value of the first process parameter and based on the second measurement signal to determine a measured value of the second process parameter;

wherein the first measurement signal and the second measurement signal serve different functions in the context of the monitoring and/or controlling of the process.

A measuring cell includes a receiving space for accommodating the respective sample, e.g. a container or a line, and at least one measuring transducer, which is embodied for registering a measured variable influencing the measurement signal of the measuring transducer for the sample accommodated in the receiving space. The measuring transducer can comprise a measuring transducer embodied to convert the measured variable into an electrical signal, which is output, in given cases, further processed, as measurement signal. The measuring transducer can, for example, contact the sample. Alternatively, it can be in contact with the sample by registering radiation emitted from the sample or by registering radiation radiated into the sample, after it has interacted with the sample; and a process medium can be, for example, a process liquid. The first and second samples can be formed from a predetermined amount of process liquid removed from the process container, by dividing such amount of removed liquid. It is also possible to withdraw the first and second samples sequentially from the process container.

Since the apparatus is embodied to determine, and to provide to the control and evaluation system, process specific measurement signals, which serve different functions in the context of the monitoring and/or controlling of the process, it is no longer necessary to provide different measuring devices for determining various parameters of different functions, wherein the measuring devices frequently also determine parameters not relevant for the particular process. The measuring cells can be relatively simply embodied and comprise, besides the receiving space and the measuring transducer, in given cases, only an on-site electronics for a first processing of the measurement signals, especially for amplification and/or digitizing. In contrast to a measurement setup, in the case of which there are combined with one another different, complete measuring devices with, in each case, their own control and evaluation systems with accompanying input means and display systems, in order to register two different parameters, in fact, a significantly compacter measurement structure is possible.

The application of a central control and evaluation system, especially a single, central control and evaluation system, which processes the two measurement signals and controls the two measuring cells, especially the two measuring transducers, permits a determining of the parameters at times close to one another and a comfortable servicing of the apparatus. Moreover, the apparatus is able to coordinate the determining of the parameters and their application for control tasks. This permits an energy and resource efficient monitoring and controlling of industrial processes and laboratory processes. If the superordinated control and evaluation system uses input means and one display system, e.g. a display, for display of measured values, device parameters and, in given cases, evaluation information, a simple and comfortable servicing of the apparatus is possible, while in the case of a measurement setup, in the case of which a number of individually operable, complete measuring devices, especially each with its own control- and evaluation system and input- and output means, are combined with one another, the servicing and the maintenance of the measurement setup are clearly more complex and require trained personnel.

Advantageous is an embodiment, in the case of which the first process parameter is a control parameter (critical process parameter, CPP), and the second process parameter is a product quality parameter (critical quality attribute, CQA) of the process.

While in the case of the procedure according to the state of the art, in the case of which the CQAs are ascertained offset in time compared with the sample taking, especially most often even only after the terminating of the process, it is advantageous to determine a selected or a few selected product quality parameters with a fully automated, process connected analytical system with a very small time offset for direct bioprocess monitoring. This does not necessarily mean that final checking of the manufactured product in the laboratory for proof of the specifications (end checking) can be omitted. In the case of near in time determining of product quality parameters, such as here provided, advantageously parallel to the processing, the maintaining of the product specifications can be checked, and in case they are not met, the process can, in given cases, be terminated early, so that no additional resources (especially time and costs of the culture media) are consumed without product yield.

Table II presents, by way of example, some important product quality-(CQA) and control parameters (CPP) to be determined in practice and possible biosensor-based measuring methods with optical and amperometric detection, as determinable with a flow through measuring system.

TABLE II

| | | | | | |
|---|---|---|---|---|---|
| Glucose | Nutrient | x | | x | CPP |
| Lactate | Metabolic product | x | | x | CPP |
| Ammonium NH$_3$/NH$_4^+$ | Metabolic product | x | | | CPP |
| Glutamine | Nutrient (Amino acid) | x | x | x | CPP |
| Other nutrients | Lactose, Galactose, Saccharose, Maltose | x | | | CPP |
| Other amino acids | Alanine, Aspartic Acid, I-Amino Acids | x | | | CPP |
| Other metabolites | Acetyl-choline, Pyruvate, Acetate, Citrate | x | | | CPP |
| Viable/dead cells | | | x | | CPP |
| Enzyme activity | Lactate dehydrogenase (LDH) activity | x | | | CQA |
| Clotting factor 8 activity | | x | | | CQA |
| Clotting factor 8 content | | | | x | CQA |
| Specific Immunglobulin (Ig) types | IgG, IgA, IgM | | (x) | x | CQA |
| Host Cell Protein | | | | x | CQA |
| Glycan structure/ Glycosyiation | Fucosylated N-glycans | | | x | CQA |
| Affinity properties | | | | x | CQA |
| Protein aggregation | | | x | | CQA |

For determining product quality, and control, parameters with the apparatus of the invention, different measuring methods and detection principles can be utilized and combined with one another. Depending on required parameters, established laboratory methods can be transferred, and/or commercially obtainable reagents-kits utilized, for automated execution in the apparatus of the invention. Especially advantageous, in such case, for simple, robust, process suitable automation is to conduct the measurements within a flow through system. Within such a system, both heterogeneous as well as also homogeneous biological assays can be performed and the measured variable suitably, most often optically, detected. Preferred, in such case, is a solid phase bound, affinity immuno sensor with the properties described in German Patent DE 201010064391 A1, German Patent DE 102010064392 A1, International Published Application WO 2012055606 A1 and International Published Application WO 2012055607 A1.

For example, analyte- or other target molecules of the assay bound on immobilized receptors can be provided with an enzyme marking, so that in the case of measuring in a flow through system a substrate, which is converted with the enzyme to a product with changed optical properties (e.g. as regards absorption or fluorescence), is transported to the analyte- or target molecules bound on the receptors, enzyme marked and the formed product transported away. Current values of the product quality, or control, parameters to be determined can be taken into consideration through evaluation of the behavior of the primary signal of the optical measurement, e.g. an absorption measurement, when the substrate solution passes through. Advantageously, the optical measurement is performed spatially isolated, especially downstream with reference to the detection region comprising the immobilized receptors.

Control parameters include, especially, metabolite contents or the fraction of viable or dead cells in question. Product quality parameters include activities, affinity properties or protein aggregation of the specific product in question. In a simple variant, also the content of the specific product can serve as CQA. In the case of an activity determination as CQA, the fraction of the active substance (=biologically active substance) is ascertained. Especially advantageous is the determining of the fraction of the active substance relative to the total content of the substance. In the case of the parameter, clotting factor 8, this is done based e.g. on an activity determined by means of a homogeneous method (especially in solution), together with a clotting factor 8-content determined by means of a solid phase bound, affinity immunoassay.

The first process parameter mentioned above can be selected from the group consisting of: a metabolite content of the sample, especially an anabolite, or catabolite, content, and a content of viable and/or dead cells.

The metabolite content can be a nutrient content or a metabolite product content. Especially, the metabolite content can be a glucose content, a lactate content, an ammonium content, a glutamine content, a lactose content, a galactose content, a sucrose content, a maltose content, an alanine content, an aspartic acid content, an l-amino-acid content, an acetylcholine content, a pyruvate content, an acetate content, a citrate content.

The second process parameter can be selected from the group consisting of: the content of the product of the process in the liquid sample, an enzyme activity, a clotting factor 8 content and activity, a content of specific immunoglobulin (Ig) types, especially an IgG-, IgA-, IgM content, a content of host cell protein, the glycosylation pattern/structure of the product, the affinity of the analyte to a target structure and protein aggregation.

In an advantageous embodiment of the invention, the first and/or the second measuring cell are/is embodied to register the corresponding measurement signal biosensor based, i.e. through use of the specific affine detection of the analyte by biological, respectively biomolecular, recognition structures. Advantageously, the first or the second measuring cell is embodied for performing a solid phase bound, immunological assay for producing its measurement signal. The respectively other measuring cell can in this embodiment produce its measurement signal without performing a solid phase bound, immunological assay, especially by application of an optical or an amperometric sensor and/or a photometric cuvette test. As already mentioned, the two measuring cells can be operable using flow through operation.

Advantageously, the first measuring cell includes at least one enzyme sensor for determining CPPs.

The apparatus can have a process connection, via which it is connectable to a bioreactor. The process connection can especially comprise an apparatus for automatic sample taking from a process container containing the process liquid and/or an apparatus for sample handling. The apparatus for sample taking can be connectable both to laboratory bioreactors as well as also to process bioreactors. It can, for example, have a sample lock for connection of a liquid transport line with the bioreactor and an apparatus for the transport of process medium through the liquid transport line from the bioreactor in the direction of the measuring cells.

The apparatus can advantageously be embodied to execute a standard addition method for determining the first or second parameter. For this, a corresponding control algorithm can be furnished in the control and evaluation system. The apparatus includes in this embodiment supplementally at least one container serving as liquid reservoir with standard liquid, which is suppliable to the liquid sample to be supplied into the receptacle of the measuring cell or to liquid sample already contained in the receptacle of the measuring cell, in order to add to the liquid sample one or more predetermined volumes of the standard liquid. The addition of standard liquid to the liquid sample can be controlled by means of one or more pumps and/or valves controlled through the control and evaluation system.

The invention relates also to a method for automated determining of at least two substances in samples of a process liquid by means of an apparatus according to the above described embodiments, wherein the determining of the first and second parameters occurs independently of one another.

The first parameter in this method can be a control parameter CPP, especially a metabolite content, determined by means of a sensor, especially an enzyme sensor and the second parameter a product quality parameter, e.g. a product content or a product activity, determined by means of a solid phase bound, affinity assay.

The first and second parameters can be determined by a repeatedly performable step sequence, which comprises the passing of one or more liquids through the measurement cells multiple times (without using manual steps) during the running of a bioprocess. Especially, the measurement signals of the first and/or second measuring cells can be produced using the flow through method. Thus especially in the case, in which the second measuring cell has enzyme sensors, the samples, in given cases, pretreated with assay reagents, are led through one of the measuring cells and the process parameters determined while the samples are flowing through the measuring cell. If a solid phase bound, affinity assay is performed in one of the measuring cells, in the case of which analyte- or other target molecules bound on immobilized receptors are provided with an enzyme marking, in the case of a flow method, a substrate, which is converted with the enzyme marking to a product with changed optical properties, can be transported to the analyte- or target molecules and the formed product transported away. The registering of the process parameter based on the optical property of the product formed from the substrate can occur directly in the detection region comprising the immobilized receptors or downstream from the detection region.

For determining the first and/or second parameter, especially for determining such as metabolite content, the standard addition method can be applied.

The apparatus of the invention, respectively the method of the invention, permits a determining of CQAs, especially product quality and/or product quantity, of a biotechnological process as well as, in given cases, simultaneously, a determining of CPPs, e.g. the content, especially the concentration, of one or more metabolites arising in the process, wherein supplementally disturbance effects can be automatically compensated. The method and the apparatus can be applied both in the laboratory as well as also in the process.

The apparatus and the method permit especially the determining of a content, especially a concentration, of a metabolite and/or a product of a bioprocess in a liquid sample taken from the bioprocess. The determining of the content of the metabolite, respectively the determining of the content of the product, in the liquid sample will, on occasion, be referenced in the following as determining of the metabolite, respectively determining of the product.

The invention has a series of advantages:

The invention permits automatic measurement within a platform, especially the integration and combination of the metabolite analysis in an immunoanalyzer embodied, for example, as a cabinet device, for modularly adaptable, target protein/product determination. A suitable platform is described, for example, in German Patent DE 201010064391 A1, German Patent DE 102010064392 A1, International Published Application WO 2012055606 A1 and International Published Application WO 2012055607 A1, to the disclosures of which comprehensive reference is taken.

The invention permits a virtually-simultaneous and virtually real time determining of the most important, quality influencing, critical process parameters (CPPs) and the product quality parameters (CQAs).

The advantages of known laboratory methods are united in an automated, analytical device suitable for process analysis.

A direct process control and optimizing is permitted by the control and evaluation system of the apparatus of the invention. Alternatively, the control and evaluation system can communicate with a control system of the process.

Through the automating, measurement inaccuracies in the case of metabolite determination through the influence of disturbance effects, above all, through matrix effects of the sample to be analyzed (pH, viscosity, ionic strength, humic materials, colored and turbid solution, etc.), can be effectively eliminated: The apparatus is advantageously embodied for applying the standard addition method for ascertaining parameters reflecting the content of a metabolite or the content of a product. This leads to a higher accuracy of measurement in comparison with the analytical devices with automated metabolite determination listed in the above Table I. In the case of application of the standard addition method, the metabolite determination of each sample occurs with its own calibration function (see further below with reference to FIG. 2).

BRIEF DESCRIPTION OF THE DRAWINGS

The invention will now be explained in greater detail in the following based on the examples of embodiments illustrated in the drawing, the figures of which show as follows.

DETAILED DISCUSSION IN CONJUNCTION WITH THE DRAWINGS

Figure 1:
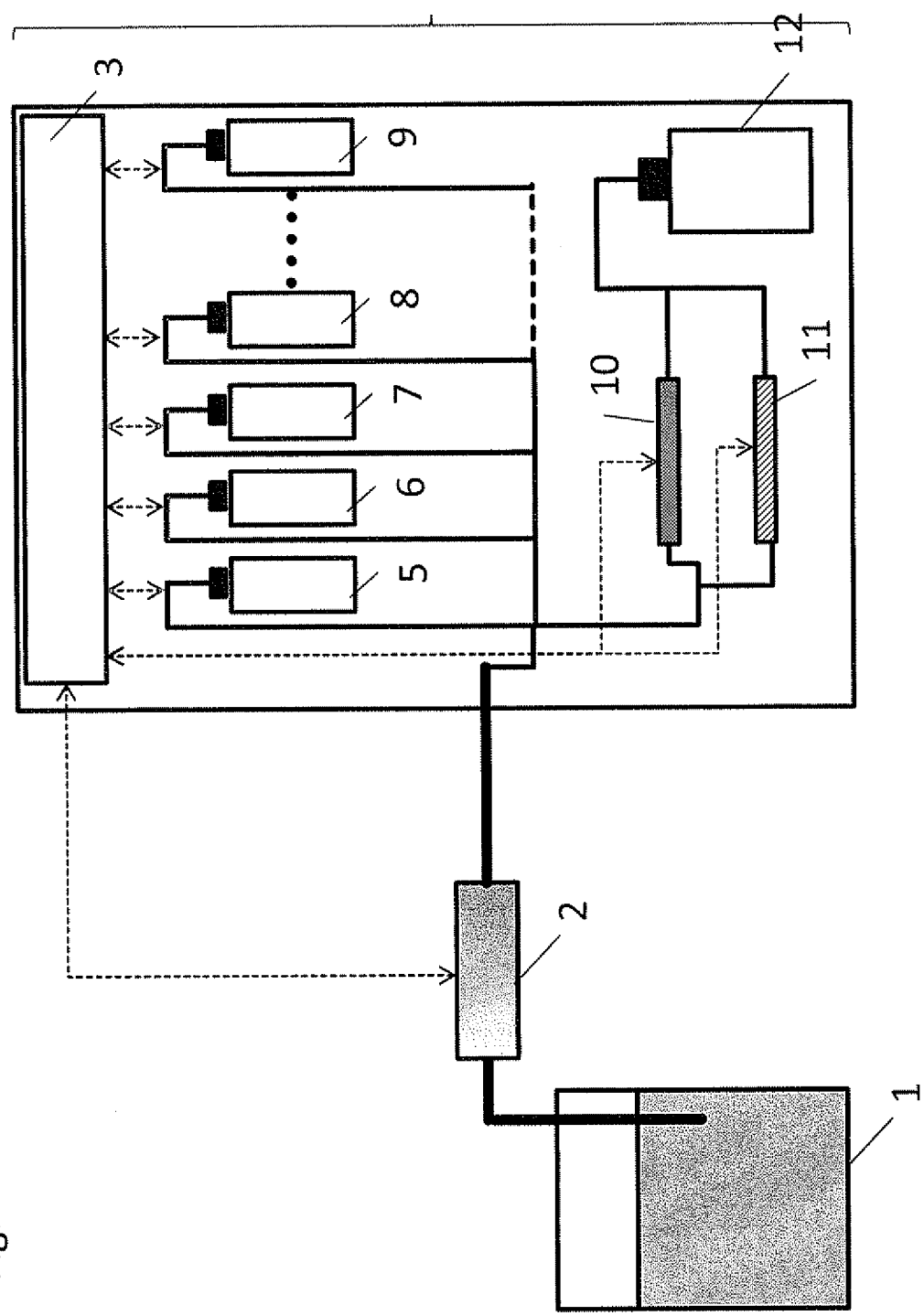
FIG. 1 is a schematic representation of an apparatus of the invention.

FIG. 1 shows an apparatus for analysis of a sample liquid. An entire analysis, or measuring cycle, occurs automatically under supervision of the central control and evaluation system 3. Taken from a process container 1 through a suitable process connection 2 and transported via liquid transport lines to measurement ready measuring cells 10, respectively 11, is sample liquid of a process serving for producing a product. The process connection 2 comprises an apparatus for automatic sample removal from the process container 1 and includes e.g. a sample lock and a liquid transport line connected with the sample lock. By means of a supply and transport system (not shown), which includes, for example, a pump, a predetermined amount of sample can be fed via the liquid transport line to the measuring cells 10 and 11. The central control and evaluation system 3 is embodied to control the sample taking via the process connection 2, for example, by controlling the sample lock and/or the supply- and transport system.

Measurement readiness was earlier assured by suitable, completely automatically running, method steps, which also include the successive feeding of the assay reagents from the supply containers 7 to 9. Also these method steps are controlled by the central control and evaluation system 3 in the example shown here. For transport of the assay reagents and, in given cases, other liquids, such as cleaning, and standard, solutions into the measuring cells 10, 11, the apparatus includes one or more liquid-transport systems, such as pumps or pneumatic pressure transmitters, which are controllable by the control and evaluation system 3. The optical or electrical measurement signal produced, in each case, by the measuring cells in the case of the measuring of the sample, and correlated to the analyte concentration of the sample, is registered by the central control and evaluation system 3.

The first measuring cell 10 serves for metabolite determination, consequently for determining a CPP. It can comprise, for example, the automated performance of an enzymatic assay in solution with photometric detection (e.g. using a commercial glucose assay kit, e.g. of Sigma Aldrich, based on glucose oxidase enzyme systems or hexokinase/glucose-6-phosphate dehydrogenase enzyme systems). In this case, the metabolite is glucose. For photometric detection, the first measuring cell 10 can comprise an optical measuring transducer, which converts the optical, photometric signal into an electrical signal, which is output to the control and evaluation system 3 as measurement signal of the measuring cell 10. Alternatively or supplementally, the first measuring cell 10 can comprise amperometric enzyme sensors (for examples, see Table I), which are embodied to produce an electrical measurement signal and to output such to the control and evaluation system 3.

The second measuring cell 11 serves for determining a product content of the liquid sample, consequently a CQA. It is based preferably on a solid phase bound, affinity immunosensor, e.g. with the properties described in German Patent DE 201010064391 A1, German Patent DE 102010064392 A1, International Published Application WO 2012055606 A1 and International Published Application WO 2012055607 A1. Especially, the second measuring cell 11 is embodied by passing through one or more of the assay reagents from selected ones of the supply containers 7 to 9 to construct a sensor matrix, which has a large number of receptors, to which an analyte to be determined in the assay to be performed in the measuring cell 11, respectively some other target molecule to be determined, is selectively and specifically bound. The measuring cell 11 is advantageously, moreover, embodied after the terminating of the assay to be automatically chemically and/or electrochemically regenerated, so that the sensor matrix can be automatically repeatedly regenerated, in order to be ready for new measurements on samples newly taken from the container 1.

The detection of the measured variable (e.g. the analyte content of the sample) to be determined with the assay is performed, for example, optically. For this, the second measuring cell 11 can comprise an optical measuring transducer, which registers a fluorescence correlated with the measured variable or an absorption correlated with the measured variable and converts such into an electrical signal, which is output to the control and evaluation system 3 as measurement signal of the second measuring cell 11.

The measuring cells can include an on-site measuring electronics, which serves for a first processing, especially for amplification and/or digitizing, of the measurement signals. A more extensive processing of the measurement signals, especially an evaluation for determining the measured variable or therefrom derived variables, is preferably executed by the control and evaluation system 3.

Advantageously, the first measuring cell 10 and the second measuring cell 11 are operable in a flow through mode. The measuring cells 10 and 11 can serve, for example, both for performing heterogeneous as well as also homogeneous biological assays, especially with optical detection of the measured variable.

The determinations with the measuring cells 10 and 11 can occur virtually simultaneously. Additional measurements for determining the metabolites can additionally occur in shorter measurement intervals than the product determination. For compensation of measurement inaccuracies in the case of the metabolite determination by means of the first measuring cell 10, inaccuracies which result from matrix influences of the sample to be analyzed, in the example shown here, the standard addition method is applied. In this regard, the supply containers 5 and 6 contain standard solutions with two respectively known concentrations of the analyte. In the example shown here, the control and evaluation system 3 serves for automatic metering and transport of predetermined volumes of the standard solutions to the sample to be analyzed.

These are added to the sample and analyzed automatically by means of the first measuring cell 10 supplementally to the sample without standard addition. All measurements occur with one and the same sample matrix. The metabolite determination of each sample occurs with its own calibration function. Changes of slope and zero point of the calibration lines in comparison to external calibrating with standard solutions with differing properties than the sample do not affect the determining. Measurement with higher accuracy can occur. All liquids end up in the waste vessel 12.

Figure 2:
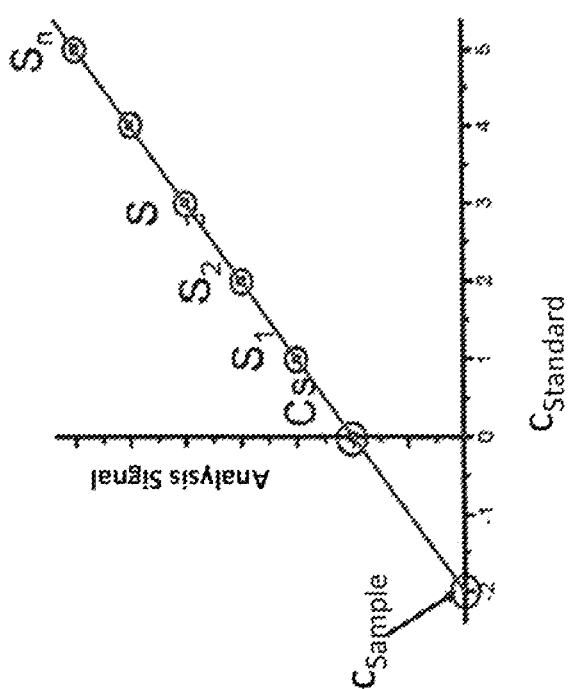
FIG. 2 is a schematic representation for explaining the standard addition method.

Based on FIG. 2, a short explanation of the standard addition method will now be given. Besides the measurement signal of the unknown sample without standard addition $C_S$, the analysis of at least one additional sample with added standard (at least $S_1$, up to $S_n$) must occur. The so obtained measurement signals plotted versus the added standard concentrations result in the relevant calibration line. After extrapolation of the function, there results from the magnitude of the zero position of the function the concentration of the unknown $c_{Sample}$. Proviso for the application of the method is that the relationship is linear in the working range.

The control and evaluation system 3 includes a data processing system and software executable thereby, which serves for performing the above described standard addition method and the analysis of liquid samples, especially the control of the apparatus and the ascertaining of values of the monitored parameters based on the measurement signals delivered from the measuring cells 10, 11. Additionally, the control and evaluation system 3 can comprise display means for display of measured values and parameters of the apparatus as well as input means for input of commands or parameters by a user.

The control and evaluation system 3 can be embodied to control a monitored bioprocess. Alternatively, it can also be embodied to output the ascertained values of the process parameters to a control unit of the monitored process. In both cases, the two parameter values determined by means of the measuring cells 10, 11 are taken into consideration for different functions, namely for control (metabolite) and for near in time monitoring of the product quality.

The invention claimed is:

1. An apparatus for an automated determining of at least two different process parameters of a process liquid of a process, comprising:
   a first measuring cell embodied to provide a first measurement signal dependent on a first process parameter of a first sample of the process liquid removed from a process container external to the apparatus, the first measuring cell including a first receiving space for accommodating the first sample, a first measuring transducer, and a first electronics embodied to amplify and to digitize the first measuring signal;
   a second measuring cell embodied to provide a second measurement signal dependent on a second process parameter of a second sample of the process liquid removed from the process container, the second measuring cell including a second receiving space for accommodating the second sample, a second measuring transducer, and a second electronics embodied to amplify and to digitize the second measuring signal; and
   a control and evaluation system embodied to receive and to process said first and second measurement signals, to determine a measured value of said first process parameter based on the first measurement signal, to determine a measured value of said second process parameter based on the second measurement signal, and to operate on the measured values to monitor and control the process,
   wherein said first measurement signal and said second measurement signal serve different functions in monitoring or controlling the process.

2. The apparatus as claimed in claim 1, wherein said first process parameter is a control parameter of the process and said second process parameter is a product quality parameter of the process.

3. The apparatus as claimed in claim 1, wherein the apparatus is embodied to measure said first and/or second process parameter within a flow through system.

4. The apparatus as claimed in claim 1, wherein said first process parameter is a metabolite content of the sample, including an anabolite or a catabolite content, is a content of viable cells in the sample, or is a content of dead cells in the sample.

5. The apparatus as claimed in claim 1, wherein said second process parameter is a content of a product of the process in the liquid sample or a product activity.

6. The apparatus as claimed in claim 1, wherein the apparatus is embodied to determine said first process parameter and/or said second process parameter by a standard addition method.

7. The apparatus as claimed in claim 1, wherein said first or said second measuring cell is embodied for performing a solid phase bound, immunological assay for producing its measurement signal.

8. The apparatus as claimed in claim 7, wherein the other measuring cell produces its measurement signal without performing a solid phase bound, immunological assay but with application of an optical sensor, an amperometric sensor, and/or a photometric cuvette test.

9. The apparatus as claimed in claim 7, wherein said first measuring cell includes at least one enzyme sensor.

10. The apparatus as claimed in claim 1, further comprising a process connection, the process connection including an apparatus for automatic sample taking and an apparatus for sample handling, wherein the first sample and the second sample are taken from the process container containing the process liquid and transported via the process connection to the first measuring cell and to the second measuring cell.

11. The apparatus as claimed in claim 10, wherein the apparatus for sample taking is connectable to laboratory bioreactors and to process bioreactors.

12. The apparatus according to claim 1, wherein the process is a bioprocess.

13. The apparatus according to claim 2, wherein the control parameter is a critical process parameter of the process and the product quality parameter is a critical quality attribute of the process.

14. The apparatus of claim 6, wherein the first process parameter or the second process parameter is a metabolite content.

15. The apparatus of claim 7, wherein the other measuring cell produces its measurement signal with application of an optical sensor or an amperometric sensor or a photometric cuvette test.

16. An apparatus for analysis of a liquid medium, comprising:
a first measuring cell including a first receiving space for a first liquid sample, a first measuring transducer, and a first electronics, wherein the first measuring transducer is embodied to generate a first measurement signal dependent on a first process parameter, and wherein the first electronics is embodied to amplify and to digitize the first measurement signal;
a second measuring cell including a second receiving space for a second liquid sample, a second measuring transducer, and a second electronics, wherein the second measuring transducer is embodied to generate a second measurement signal dependent on a second process parameter, and wherein the second electronics is embodied to amplify and to digitize the second measurement signal;
a process connection including a sample lock, liquid transport lines, and a pump, wherein the process connection is connectable to a process container external to the apparatus, wherein the process connection is configured to remove a desired amount of liquid from the process container and to transport the desired amount of liquid from the process container to the first measuring cell and to the second measuring cell;
a plurality of reagent supply tanks, wherein the supply tanks are connected via liquid transport lines to the first measuring cell and to the second measuring cell;
a control unit embodied to receive and to process the first digital measurement signal and the second digital measurement signal and to control the operation of the apparatus; and
a cabinet, wherein the first measuring cell, the second measuring cell, the plurality of supply tanks, and the control unit are disposed within the cabinet.

* * * * *